United States Patent
Zhao et al.

(10) Patent No.: US 10,400,203 B2
(45) Date of Patent: Sep. 3, 2019

(54) METHOD FOR PRODUCING LIVING TISSUE AND ORGAN

(71) Applicant: SHENZHEN EXCELLENT TECHNOLOGY LIMITED LIABILITY COMPANY, Guangdong (CN)

(72) Inventors: Xiaowen Zhao, Guangdong (CN); Dongfeng Zhang, Guangdong (CN); Wenping Zhao, Guangdong (CN); Junhua Cai, Guangdong (CN)

(73) Assignee: SHENZHEN EXCELLENT TECHNOLOGY LIMITED LIABILITY COMPANY (CN)

( * ) Notice: Subject to any disclaimer, the term of this patent is extended or adjusted under 35 U.S.C. 154(b) by 18 days.

(21) Appl. No.: 15/768,283

(22) PCT Filed: Jul. 13, 2016

(86) PCT No.: PCT/CN2016/089892
§ 371 (c)(1),
(2) Date: Apr. 13, 2018

(87) PCT Pub. No.: WO2017/063412
PCT Pub. Date: Apr. 20, 2017

(65) Prior Publication Data
US 2018/0298315 A1   Oct. 18, 2018

(30) Foreign Application Priority Data
Oct. 14, 2015   (CN) .......................... 2015 1 0656144

(51) Int. Cl.
*C12M 1/00*   (2006.01)
*C12M 3/00*   (2006.01)
(Continued)

(52) U.S. Cl.
CPC .............. *C12M 21/08* (2013.01); *B33Y 50/02* (2014.12); *B33Y 80/00* (2014.12); *C12M 25/00* (2013.01);
(Continued)

(58) Field of Classification Search
CPC ......... B33Y 50/02; B33Y 80/00; B33Y 10/00; C12M 21/08; C12M 25/00; C12M 33/00; G06T 17/00; G06T 17/10; G16H 30/40
See application file for complete search history.

(56) References Cited

U.S. PATENT DOCUMENTS

| 8,412,503 B2* | 4/2013 | Yamamoto .......... G06F 17/5018 703/11 |
| 2010/0104156 A1* | 4/2010 | Yoshida ................ G06T 7/0012 382/128 |

(Continued)

FOREIGN PATENT DOCUMENTS

| CN | 104146793 A | 11/2014 |
| CN | 104382670 A | 3/2015 |
| CN | 105574927 A | 5/2016 |

OTHER PUBLICATIONS

International Search Report dated Oct. 12, 2016; International Patent Application No. PCT/CN2016/089892 filed on Jul. 13, 2016; ISA/CN.

*Primary Examiner* — Edward Park
(74) *Attorney, Agent, or Firm* — McDonald Hopkins LLC

(57) ABSTRACT

A method for producing a living tissue and organ includes: collecting medical image information of a target tissue and organ, and converting the medical image information into three-dimensional image information; performing machine recognition and multiple feature comparisons on the three-dimensional image information, and generating a primary three-dimensional model according to physiological structure data of tissues and organs in a tissue and organ database
(Continued)

and a residual profile of the target tissue and organ; generating a complete three-dimensional model by producing an internal microstructure of the primary three-dimensional model with reference to the tissue and organ database; producing a full-scale physical model based on the complete three-dimensional model by an additive manufacturing process; and performing a living cell-based tissue reconstruction in the full-scale physical model to produce a living tissue and organ.

18 Claims, 3 Drawing Sheets

(51) Int. Cl.
*G06T 17/00* (2006.01)
*B33Y 50/02* (2015.01)
*B33Y 80/00* (2015.01)
*G16H 30/40* (2018.01)
*C12M 1/12* (2006.01)
*G06T 17/10* (2006.01)
*C12M 1/26* (2006.01)
*B33Y 10/00* (2015.01)

(52) U.S. Cl.
CPC ............ *C12M 33/00* (2013.01); *G06T 17/00* (2013.01); *G06T 17/10* (2013.01); *G16H 30/40* (2018.01); *B33Y 10/00* (2014.12)

(56) References Cited

U.S. PATENT DOCUMENTS

2013/0259345 A1* 10/2013 El-Baz .................. G06T 7/0012
　　　　　　　　　　　　　　　　　　　　　　　　382/131
2015/0025316 A1* 1/2015 Hasegawa ................ A61B 1/04
　　　　　　　　　　　　　　　　　　　　　　　　600/109

* cited by examiner

METHOD FOR PRODUCING LIVING TISSUE AND ORGAN

CROSS-REFERENCE TO RELATED APPLICATION

This application is a 35 U.S.C. 371 national stage filing of PCT Application No. PCT/CN2016/089892 filed on Jul. 13, 2016, which claims priority to Chinese Patent Application No. 201510656144.7 filed on Oct. 14, 2015, each of which are incorporated herein in their entirety by reference.

TECHNICAL FIELD

The present disclosure relates to the field of biomedicine, and particularly relates to a method for producing a living tissue and organ.

BACKGROUND

Exhaustion and injury of tissues and organs are major problems in clinical medicine. A therapy for the exhaustion and injury of tissues and organs mainly includes organ transplantation, surgical repair, artificial substitutes, medical instruments and drug treatment. Autologous organ transplantation is a conventional therapy method which might lead to a new wound, is limited in donor sites and seriously lacks of donor organs. On the other hand, artificial substitutes have a problem of biocompatibility. In recent years, the tissue engineering technology emerges to effectively avoid the above disadvantages, and increasingly becomes a widely recognized medical therapy method.

To achieve repair and reconstruction, the tissue engineering utilizes principles and methods of engineering science and biological science to adhere normal tissue cells cultured and proliferated in vitro to a biomaterial scaffold with good biocompatibility which can be absorbed by an organism, transplant a composite of the cells and the biomaterial into an injured part of an organism and form a substitute consistent with the injured tissue and organ in forms and functions by the cells in a process during which the biomaterial scaffold is gradually absorbed and degraded by the organism. Clinical application of the tissue engineering is primary in treatment of tissue injury and organ exhaustion. A traditional therapy mainly includes implementing allotransplantation, implementing surgical reconstruction and using an artificial organ. Allotransplantation is very limited in donor sources, and essential immunosuppressive treatment easily leads to other diseases. Due to inapplicability of autologous tissues, surgical reconstruction is not ideal in treatment effects, and a surgical procedure is complex. The artificial organ can only provide partial functions, and has long-term dependence on drugs, thereby influencing quality of life of a patient and bringing high medical expenses.

The following problem is popular in a scaffold for the tissue engineering made in recent years: a tissue is rapidly formed on an outer edge of the scaffold while a nutrient solution and cells fail to enter the center of the scaffold, causing necrosis of a substitute part. Many methods can be used to prepare the scaffold for tissue engineering. Traditional methods include fiber bonding, solvent casting/particulate leaching, melting, gas foaming, phase separation, microsphere sintering and the like. Although these traditional methods can obtain a successful scaffold for tissue engineering, the performance of the scaffold for tissue engineering obtained by these traditional methods is not ideal in the following aspects: lack of mechanical strength, low degree of interpenetration of pores and poor controllability of porosity and pore distribution. As a result, cell growth and vascularization of the tissue are influenced. Regardless of the method used, the prepared scaffolds have no consistent internal structure, and external structures of the scaffolds do not coincide with anatomical structures of injured tissues and organs of the patients, causing that individualized manufacturing and production requirements for the scaffolds cannot be achieved.

To solve technical bottlenecks of artificial living tissues and organs in the related art, the present disclosure provides a method for producing a living tissue and organ. According to the method, problems such as lacking of donor organs, biological anisotropy in a transplantation process and the like are solved. The method is applicable to clinic, scientific research, teaching experiments and the like. The method can fill a blank of the relevant technology and can also generate great social benefits and economic benefits.

SUMMARY

The present disclosure provides a method for producing a living tissue and organ, including:

collecting medical image information of a target tissue and organ, and converting the medical image information into three-dimensional image information;

performing machine recognition and multiple feature comparisons on the three-dimensional image information, and generating a primary three-dimensional model according to physiological structure data of tissues and organs in a tissue and organ database and a residual profile of the target tissue and organ;

generating a complete three-dimensional model by producing an internal microstructure of the primary three-dimensional model with reference to the tissue and organ database;

producing a full-scale physical model based on the complete three-dimensional model by an additive manufacturing process;

performing surface treatment on the full-scale physical model, and verifying geometrical shapes and functions of an internal three-dimensional microstructure and an appearance three-dimensional structure of the full-scale physical model;

performing a medical biological test on the full-scale physical model to determine whether the full-scale physical model satisfies a medical microenvironment in which a living cell multiplies if the full-scale physical model meets a preset verification requirement; and performing a living cell-based tissue reconstruction in the full-scale physical model to produce a living tissue and organ if the full-scale physical model satisfies the medical microenvironment.

Optionally, the full-scale physical model is made of materials with biocompatibility and bioactivity.

Optionally, the materials with biocompatibility and bioactivity include: hydroxyapatite, polylactic acid and polylactic-co-glycolic acid.

Optionally, the producing a full-scale physical model based on the complete three-dimensional model by an additive manufacturing process includes producing the full-scale physical model by a three dimensional (3D) printing method.

Optionally, the producing an internal microstructure of the primary three-dimensional model includes producing the internal microstructure of the primary three-dimensional model according to porosity, aperture size and shape, and structural features.

Optionally, the verifying geometrical shapes and functions of an internal three-dimensional microstructure and an appearance three-dimensional structure of the full-scale physical model includes:

measuring parameters of the internal three-dimensional microstructure of the full-scale physical model, comparing the parameters with parameters of an internal three-dimensional microstructure of the target tissue and organ to obtain a comparison result, and determining whether the comparison result satisfies a preset requirement; and matching the appearance three-dimensional structure of the full-scale physical model with the residual profile of the target tissue and organ to determine whether a preset matching requirement is met.

Optionally, the performing surface treatment on the full-scale physical model includes disinfecting a surface of the full-scale physical model.

Optionally, after generating the complete three-dimensional model, the method further includes: storing the complete three-dimensional model as a file of at least one of the following data formats: stl, stp, obj, max, 3ds, ma, vtk and igs.

Optionally, the internal three-dimensional microstructure of the full-scale physical model includes micropores, and quantity, sizes, distribution and shapes of the micropores are adjustable.

Optionally, the internal three-dimensional microstructure of the full-scale physical model includes a pipeline structure, and distribution, pipe diameter and porosity of the pipeline structure are adjustable.

Optionally, the internal three-dimensional microstructure of the living tissue and organ includes a set of runner systems which are mutually communicated.

Optionally, the collecting medical image information of a target tissue and organ includes: collecting medical image information of the target tissue and organ of a patient through computed tomography (CT), magnetic resonance imaging (MRI) or positron emission tomography-computed tomography (PET-CT).

Compared with the related art, the living tissue and organ of the present disclosure is made rapidly, precise in the shape of the internal microstructure, high in bionic degree, small in biological anisotropy and good in medical and biological characteristics, and thus can fill a blank of the relevant technology and can also generate great social benefits and economic benefits.

DETAILED DESCRIPTION

Embodiments of the present disclosure are described with reference to the drawings. The present disclosure is described below in combination with FIG. 1 to FIG. 5. FIG. 5 is a flow chart illustrating a method for producing a living tissue and organ according to an embodiment of the present disclosure. As shown in FIG. 5, the method for producing a living tissue and organ according to the present embodiment includes operations described below.

In S110, medical image information of a target tissue and organ is collected, and the medical image information is converted into three-dimensional image information.

Figure 1:
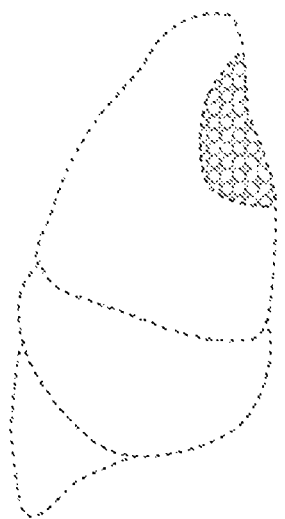
FIG. 1 is a three-dimensional structural diagram illustrating a target tissue and organ obtained according to individual medical image information.

Optionally, the medical image information of the target tissue and organ may refer to medical image information of the target tissue and organ of a patient. Optionally, the medical image information of the target tissue and organ may be medical image information of the target tissue and organ of the patient collected through computed tomography (CT), magnetic resonance imaging (MRI) or positron emission tomography-computed tomography (PET-CT). Exemplarily, FIG. 1 is a three-dimensional structural diagram illustrating a target tissue and organ obtained according to individual medical image information (i.e., medical image information of the target tissue and organ).

In S120, machine recognition and multiple feature comparisons are performed on the three-dimensional image information, and a primary three-dimensional model is generated according to physiological structure data of tissues and organs in a tissue and organ database and a residual profile of the target tissue and organ.

Figure 2:
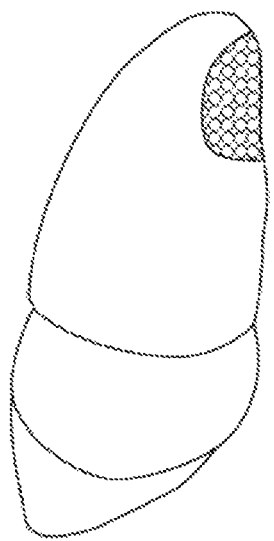
FIG. 2 is a three-dimensional structural diagram illustrating a target tissue and organ obtained according to historical data of a group.

Exemplarily, FIG. 2 is a three-dimensional structural diagram illustrating a target tissue and organ obtained according to historical data of a group, where the historical data of the group may be physiological structure data of the tissues and organs in the tissue and organ database.

In S130, an internal microstructure of the primary three-dimensional model is produced with reference to the tissue and organ database to generate a complete three-dimensional model.

Figure 3:
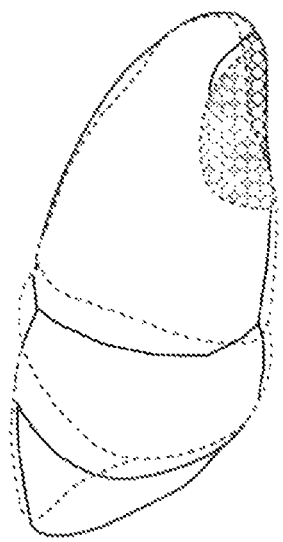
FIG. 3 is a three-dimensional structural diagram illustrating a target tissue and organ obtained by combining individual medical image information and historical data of a group.

Exemplarily, FIG. 3 is a three-dimensional structural diagram (i.e., a complete three-dimensional model) illustrating a target tissue and organ obtained by combining individual medical image information and historical data of a group.

Optionally, the internal microstructure of the primary three-dimensional model is produced according to porosity, aperture size and shape, and structural features.

Optionally, an internal three-dimensional microstructure of a full-scale physical model includes micropores, and quantity, sizes, distribution and shapes of the micropores are adjustable.

Optionally, the internal three-dimensional microstructure of the full-scale physical model includes a pipeline structure, and distribution, pipe diameter and porosity of the pipeline structure are adjustable.

Optionally, after the complete three-dimensional model is generated, the method further includes storing the complete three-dimensional model as a file of at least one of the following data formats: stl, stp, obj, max, 3ds, ma, vtk and igs.

In S140, a full-scale physical model is produced based on the complete three-dimensional model by an additive manufacturing process.

Optionally, the full-scale physical model is made of materials with biocompatibility and bioactivity. Optionally, the materials with biocompatibility and bioactivity may include: hydroxyapatite (HA), polylactic acid (PLA) and polylactic-co-glycolic acid (PLGA), which are not specifically limited.

Optionally, the full-scale physical model is produced by using a 3D printing method in S140.

In S150, surface treatment is performed on the full-scale physical model, geometrical shapes and functions of an internal three-dimensional microstructure and an appearance three-dimensional structure of the full-scale physical model are verified.

Figure 4:
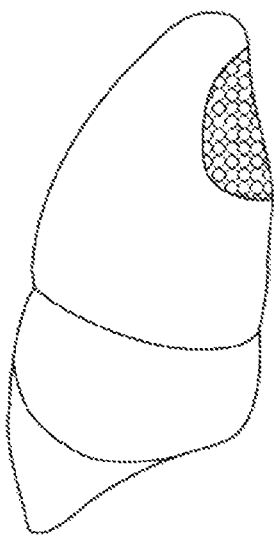
FIG. 4 is a three-dimensional structural diagram illustrating a target tissue and organ being treated and verified.
Figure 5:
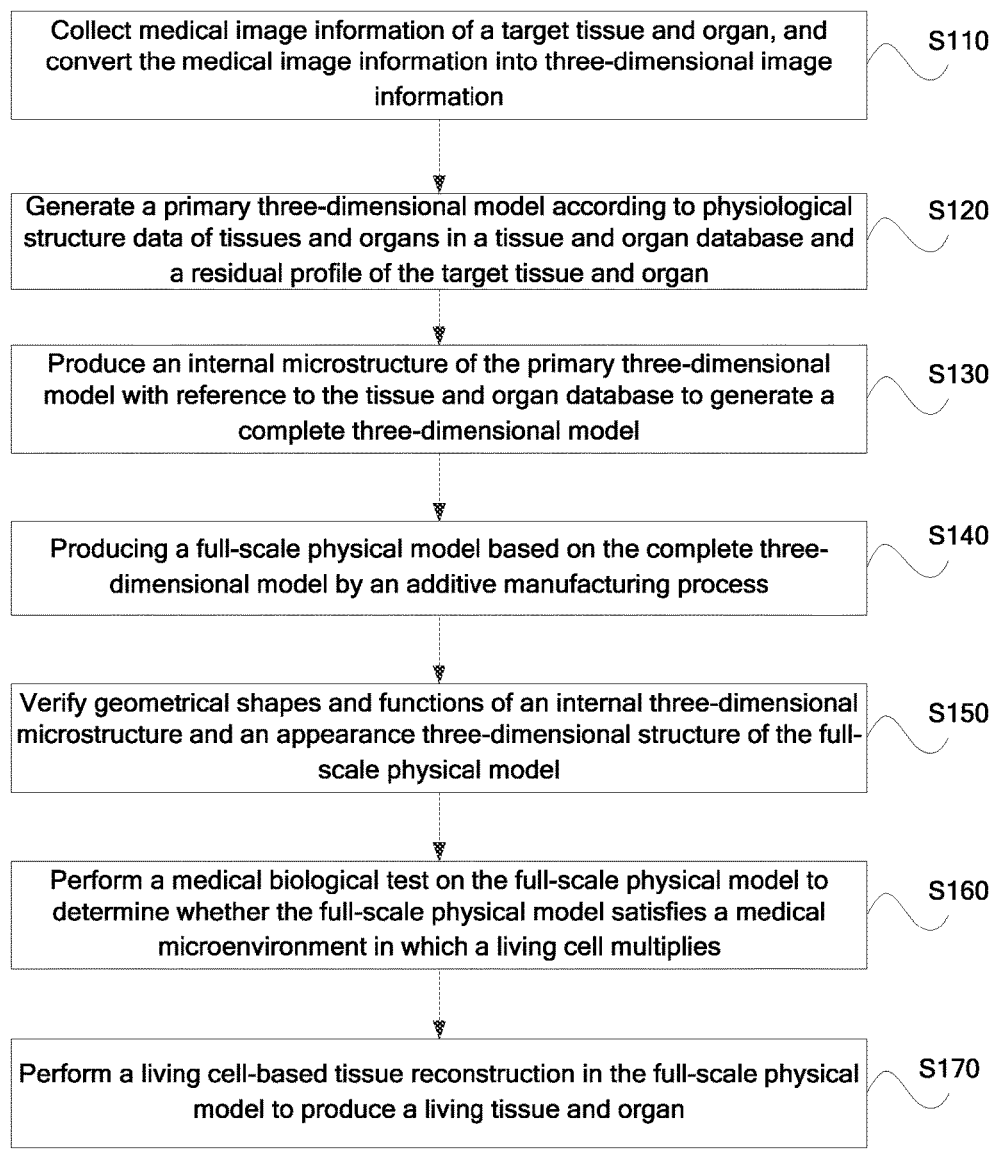
FIG. 5 is a flow chart illustrating a method for producing a living tissue and organ according to an embodiment of the present disclosure.

Exemplarily, FIG. 4 is a three-dimensional structural diagram illustrating a target tissue and organ being treated and verified. FIG. 4 exemplarily illustrates the three-dimensional structural diagram of the full-scale physical model after surface treatment and verification of the geometrical shapes and the functions are performed.

Optionally, the surface treatment on the full-scale physical model includes disinfecting a surface of the full-scale physical model. For example, the surface of the full-scale physical model is disinfected by using alcohol.

Optionally, the geometrical shapes and functions of the internal three-dimensional microstructure and the appearance three-dimensional structure of the full-scale physical model are verified by the following steps:

measuring parameters of the internal three-dimensional microstructure of the full-scale physical model, comparing the parameters with parameters of the internal three-dimensional microstructure of the target tissue and organ to obtain a comparison result, and determining whether the comparison result satisfies a preset requirement; and matching the appearance three-dimensional structure of the full-scale physical model with the residual profile of the target tissue and organ to determine whether a preset matching requirement is met.

In S160, if the full-scale physical model meets a preset verification requirement, a medical biological test is performed on the full-scale physical model to determine whether the full-scale physical model satisfies a medical microenvironment in which a living cell multiplies.

The living cell is cultured on the full-scale physical model. In a growth process of the living cell, the full-scale physical model will be gradually decomposed and absorbed by the living cell, and a living tissue and organ formed by living cell multiplication reproduces the configuration of the full-scale physical model.

In S170, a living cell-based tissue reconstruction is performed in the full-scale physical model to produce a living tissue and organ if the full-scale physical model satisfies the medical microenvironment.

Optionally, the internal three-dimensional microstructure of the living tissue and organ includes a set of runner systems which are mutually communicated.

According to the method for producing a living tissue and organ proposed by the embodiment of the present disclosure, the living tissue and organ is produced rapidly; the living tissue and organ is precise in the shape of the internal microstructure, high in bionic degree, has small biological anisotropy and good medical and biological characteristics. Therefore, the method for producing a living tissue and organ proposed by the embodiment of the present disclosure fills a blank of the relevant technology and can also generate great social benefits and economic benefits.

The above only describes disclosed embodiments, and does not limit the present disclosure in any form. Any amendment, change and equivalent variation made to above embodiments according to the substance of the present disclosure still belong to a protection scope of a technology of the present disclosure.

INDUSTRIAL APPLICABILITY

According to the method for producing a living tissue and organ proposed by the embodiment of the present disclosure, the living tissue and organ is produced rapidly; the living tissue and organ is precise in the shape of the internal microstructure, high in bionic degree, and has small biological anisotropy and good medical and biological characteristics. Therefore, the method for producing a living tissue and organ proposed by the embodiment of the present disclosure fills a blank of the relevant technology and can also generate great social benefits and economic benefits.

What is claimed is:

1. A method for producing a living tissue and organ, comprising:

collecting medical image information of a target tissue and organ, and converting the medical image information into three-dimensional image information;

performing machine recognition and multiple feature comparisons on the three-dimensional image information, and generating a primary three-dimensional model according to physiological structure data of tissues and organs in a tissue and organ database and a residual profile of the target tissue and organ;

generating a complete three-dimensional model by producing an internal microstructure of the primary three-dimensional model with reference to the tissue and organ database;

producing a full-scale physical model based on the complete three-dimensional model by an additive manufacturing process;

performing surface treatment on the full-scale physical model, and verifying geometrical shapes and functions of an internal three-dimensional microstructure and an appearance three-dimensional structure of the full-scale physical model;

performing a medical biological test on the full-scale physical model to determine whether the full-scale physical model satisfies a medical microenvironment in which a living cell multiplies if the full-scale physical model meets a preset verification requirement for geometrical shapes and a preset verification requirement for functions; and performing a living cell-based tissue reconstruction in the full-scale physical model to produce a living tissue and organ if the full-scale physical model satisfies the medical microenvironment.

2. The method for producing a living tissue and organ according to claim 1, wherein the full-scale physical model is made of materials with biocompatibility and bioactivity.

3. The method for producing a living tissue and organ according to claim 2, wherein the materials with biocompatibility and bioactivity comprise: hydroxyapatite, polylactic acid and polylactic-co-glycolic acid.

4. The method for producing a living tissue and organ according to claim 2, wherein the producing a full-scale physical model based on the complete three-dimensional model by an additive manufacturing process comprises producing the full-scale physical model by a three dimensional (3D) printing method.

5. The method for producing a living tissue and organ according to claim 1, wherein the producing a full-scale physical model based on the complete three-dimensional model by an additive manufacturing process comprises producing the full-scale physical model by a three dimensional (3D) printing method.

6. The method for producing a living tissue and organ according to claim 1, wherein the producing an internal microstructure of the primary three-dimensional model comprises producing the internal microstructure of the primary three-dimensional model according to porosity, aperture size and shape, and structural features.

7. The method for producing a living tissue and organ according to claim 6, wherein an internal three-dimensional microstructure of the living tissue and organ comprises a set of runner systems which are mutually communicated.

8. The method for producing a living tissue and organ according to claim 1, wherein the verifying geometrical shapes and functions of an internal three-dimensional microstructure and an appearance three-dimensional structure of the full-scale physical model comprises:
  measuring parameters of the internal three-dimensional microstructure of the full-scale physical model, comparing the parameters with parameters of an internal three-dimensional microstructure of the target tissue and organ to obtain a comparison result, and determining whether the comparison result satisfies a preset requirement; and
  matching the appearance three-dimensional structure of the full-scale physical model with the residual profile of the target tissue and organ to determine whether a preset matching requirement is met.

9. The method for producing a living tissue and organ according to claim 8, wherein the internal three-dimensional microstructure of the full-scale physical model comprises micropores, and quantity, sizes, distribution and shapes of the micropores are adjustable.

10. The method for producing a living tissue and organ according to claim 9, wherein an internal three-dimensional microstructure of the living tissue and organ comprises a set of runner systems which are mutually communicated.

11. The method for producing a living tissue and organ according to claim 8, wherein the internal three-dimensional microstructure of the full-scale physical model comprises a pipeline structure, and distribution, pipe diameter and porosity of the pipeline structure are adjustable.

12. The method for producing a living tissue and organ according to claim 11, wherein an internal three-dimensional microstructure of the living tissue and organ comprises a set of runner systems which are mutually communicated.

13. The method for producing a living tissue and organ according to claim 8, wherein an internal three-dimensional microstructure of the living tissue and organ comprises a set of runner systems which are mutually communicated.

14. The method for producing a living tissue and organ according to claim 1, wherein the performing surface treatment on the full-scale physical model comprises disinfecting a surface of the full-scale physical model.

15. The method for producing a living tissue and organ according to claim 14, wherein an internal three-dimensional microstructure of the living tissue and organ comprises a set of runner systems which are mutually communicated.

16. The method for producing a living tissue and organ according to claim 1, further comprising the following step after generating the complete three-dimensional model: storing the complete three-dimensional model as a file of at least one of the following data formats: stl, stp, obj, max, 3ds, ma, vtk and igs.

17. The method for producing a living tissue and organ according to claim 16, wherein an internal three-dimensional microstructure of the living tissue and organ comprises a set of runner systems which are mutually communicated.

18. The method for producing a living tissue and organ according to claim 1, wherein the collecting medical image information of a target tissue and organ comprises: collecting medical image information of the target tissue and organ of a patient through computed tomography (CT), magnetic resonance imaging (MRI) or positron emission tomography-computed tomography (PET-CT).

\* \* \* \* \*